United States Patent
Speier et al.

(10) Patent No.: US 11,092,660 B2
(45) Date of Patent: Aug. 17, 2021

(54) PILOT TONE IDENTIFICATION

(71) Applicant: Siemens Healthcare GmbH, Erlangen (DE)

(72) Inventors: Peter Speier, Erlangen (DE); Markus Vester, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/679,677

(22) Filed: Nov. 11, 2019

(65) Prior Publication Data

US 2020/0166597 A1 May 28, 2020

(30) Foreign Application Priority Data

Nov. 27, 2018 (DE) .......................... 102018220351.2

(51) Int. Cl.
| | | |
|---|---|---|
| *G01R 33/567* | (2006.01) | |
| *G01R 33/54* | (2006.01) | |
| *A61B 5/055* | (2006.01) | |
| *H04B 13/00* | (2006.01) | |

(52) U.S. Cl.
CPC .......... *G01R 33/5673* (2013.01); *A61B 5/055* (2013.01); *G01R 33/543* (2013.01); *H04B 13/005* (2013.01)

(58) Field of Classification Search
CPC .. G01R 33/5673; G01R 33/543; A61B 5/055; H04B 13/005
See application file for complete search history.

(56) References Cited

U.S. PATENT DOCUMENTS

| | | | | |
|---|---|---|---|---|
| 8,994,374 | B2 * | 3/2015 | Albsmeier | ......... G01R 33/3692 324/322 |
| 9,954,700 | B2 * | 4/2018 | Oppelt | .............. H04W 72/0453 |
| 2012/0249140 | A1 * | 10/2012 | Albsmeier | ......... G01R 33/3692 324/309 |

(Continued)

FOREIGN PATENT DOCUMENTS

| | | |
|---|---|---|
| DE | 102015203385 A1 | 8/2016 |
| DE | 102015224158 A1 | 6/2017 |

(Continued)

OTHER PUBLICATIONS

German Office Action for German Application No. 10 2018 220 351.2 dated Aug. 6, 2019.

(Continued)

*Primary Examiner* — Dixomara Vargas
(74) *Attorney, Agent, or Firm* — Lempia Summerfield Katz LLC

(57) ABSTRACT

The disclosure relates to a medical image acquisition device with a pilot tone transmitter and a pilot tone receiver and to a method for operating the same. The pilot tone transmitter is configured to emit an electromagnetic radio frequency signal into a patient. The pilot tone receiver is configured to receive the radio frequency signal and to decode an item of information relating to a physiological process in the patient. The pilot tone transmitter has a modulator configured to modulate the electromagnetic radio frequency signal with a code and the pilot tone receiver is configured to select the modulated radio frequency signal using the encoding from a plurality of signals.

17 Claims, 2 Drawing Sheets

(56) References Cited

U.S. PATENT DOCUMENTS

| | | | |
|---|---|---|---|
| 2015/0207653 A1* | 7/2015 | Oppelt | H04W 72/0453 |
| | | | 370/329 |
| 2016/0245888 A1 | 8/2016 | Bollenbeck | |
| 2017/0160367 A1 | 6/2017 | Schröter | |
| 2017/0176552 A1 | 6/2017 | Reykowski | |
| 2018/0045801 A1 | 2/2018 | Speier | |
| 2018/0172784 A1 | 6/2018 | Brunner | |
| 2018/0299522 A1* | 10/2018 | Biber | G01R 33/3692 |
| 2019/0377051 A1* | 12/2019 | Bacher | G16H 40/63 |
| 2020/0110145 A1* | 4/2020 | Zeller | A61B 5/113 |
| 2020/0150201 A1* | 5/2020 | Dornberger | G01R 33/3657 |
| 2020/0249292 A1* | 8/2020 | Biber | G01R 33/4818 |
| 2020/0333419 A1* | 10/2020 | Zhang | A61B 5/7207 |
| 2020/0396112 A1* | 12/2020 | Biber | G01R 33/3607 |
| 2021/0085260 A1* | 3/2021 | Schneider | G16H 30/40 |

FOREIGN PATENT DOCUMENTS

| | | |
|---|---|---|
| DE | 102016215044 A1 | 2/2018 |
| EP | 3098617 A1 | 11/2016 |
| WO | WO2015150953 A1 | 10/2015 |

OTHER PUBLICATIONS

Schroeder, Lea, et al. "A novel method for contact-free cardiac synchronization using the pilot tone navigator." 24th ISMRM Annual Meeting and Exhibition. 2016. pp. 1-3.

* cited by examiner

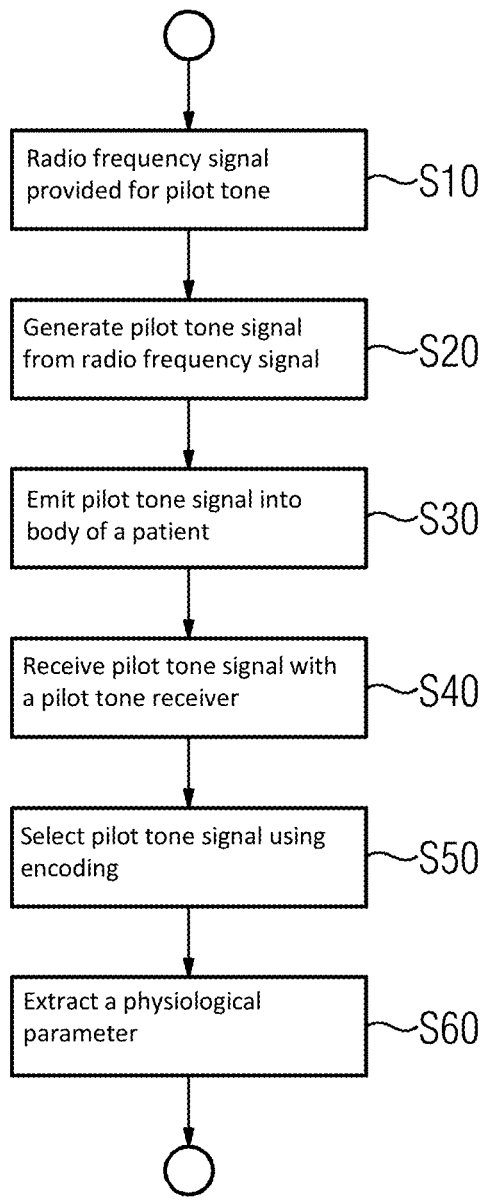

PILOT TONE IDENTIFICATION

The present patent document claims the benefit of German Patent Application No. 10 2018 220 351.2, filed Nov. 27, 2018, which is hereby incorporated by reference.

TECHNICAL FIELD

The disclosure relates to a medical image acquisition device with a pilot tone transmitter and a pilot tone receiver. The pilot tone transmitter is configured to emit an electromagnetic radio frequency signal into a patient. The pilot tone receiver is configured to receive the radio frequency signal and to decode an item of information relating to a physiological process in the patient.

BACKGROUND

Magnetic resonance tomographs are imaging apparatuses which, for imaging an examination object, orient nuclear spins of the examination object with a strong external magnetic field and by a magnetic alternating field, excite them to precession about this orientation. The precession or return of the spins from this excited state into a state with less energy in turn generates, as a response, a magnetic alternating field which is received by way of antennas.

With the aid of magnetic gradient fields, a spatial encoding is impressed onto the signals, which then permits an assignment of the received signal to a volume element. The received signal is then evaluated, and a three-dimensional imaging representation of the examination object is provided.

Depending on the pulse sequence used, also referred to as sequence, image acquisition in a magnetic resonance tomography system requires a number of milliseconds up to seconds, wherein a longer acquisition time may result in minimal noise artifacts. It is therefore expedient to start the image acquisition in each case at the start of a phase, in which the body remains relatively still, in order to avoid motion artifacts due to a movement during the image acquisition. Unavoidable movements may include the breathing and the heartbeat of the examination object. However, a phase of relative rest, for instance, after breathing out or a contraction of the cardiac muscle here also follows a phase with movements. An image acquisition in this phase is to expect a relatively long time frame with few movements so that the best measurement results are to be expected here.

It is fundamentally already known here to acquire the movements using mechanical sensors or by electrodes, for instance, which measure the excitation potentials of the muscles.

The publication DE 10 2015 203 385 describes a basic method of acquiring movements using a radio frequency signal. Here the signal is permanently acquired in a patient recording of a magnetic resonance tomograph and signal changes as a result of movements, for instance as a result of changing interferences or damping, are evaluated. A movement of the patient, caused by breathing or heartbeat, may then be identified from certain patterns of this signal.

The publication WO 2015/150953 A1 discloses a transmitter for emitting a synchronization signal, the two antennas of which are arranged at the ends of a patient leadthrough. A pilot tone may also be emitted here as a synchronization signal.

The publication DE 10 2015 224 158 describes a transmitter for pilot tone navigation in a magnetic resonance tomograph and a method for identifying a movement of a patient. The transmitter has a power supply and an antenna. The transmitter is configured to transmit a pilot tone signal by way of the antenna. The transmitter also has a decoupling element, in order to protect the transmitter output from signals which the antenna receives during magnetic resonance tomography with excitation pulses of the magnetic resonance tomograph. In the method, movement-dependent changes to the pilot tone signal of the transmitter are identified by a controller of the magnetic resonance tomograph.

SUMMARY AND DESCRIPTION

The object is therefore to improve the application of a pilot tone signal.

The object is achieved by a medical image acquisition device and a method. The scope of the present disclosure is defined solely by the appended claims and is not affected to any degree by the statements within this summary. The present embodiments may obviate one or more of the drawbacks or limitations in the related art.

The medical image acquisition device has a pilot tone transmitter and a pilot tone receiver. The pilot tone transmitter is configured to emit an electromagnetic radio frequency signal into a patient. The radio frequency signal of the pilot tone transmitter is also referred to below as pilot tone signal. The power of the pilot tone signal emitted by the pilot tone transmitter is less than 1 W, 100 mW, 10 mW, or 1 mW for instance. The pilot tone receiver is configured to receive the radio frequency signal of the pilot tone transmitter and to decode an item of information relating to a physiological process in the patient. The pilot tone transmitter has a modulator configured to modulate the electromagnetic radio frequency signal with a code. The code is configured to render the pilot tone signal clearly distinguishable from other radio frequency signals in the image acquisition device. The code may also be configured to encode a phase relationship of the modulated pilot tone signal, so that when the pilot tone signal is received, a phase shift as a result of the transmission may be detected. The pilot tone receiver is configured to select the modulated radio frequency signal by encoding from a plurality of radio frequency signals. The pilot tone receiver may be configured to deduce a change in amplitude and/or a phase shift as a result of the transmission or as a result of the body of the patient from the received pilot tone signal.

The method for operating a medical image acquisition device has the act of generating a pilot tone signal by modulating a radio frequency signal with a code through the pilot tone transmitter by its modulator. Here the radio frequency signal may be generated by the pilot tone transmitter itself by an oscillator or from a supplied signal, for instance, by mixing, multiplication, or amplification. The encoding may lie, for instance, in the frequency and/or phase of the pilot tone signal but encoding using a signal or bit sequence is also conceivable, however.

In another act, the pilot tone transmitter transmits the pilot tone signal into a body of a patient. The pilot tone transmitter may to this end have an antenna or have a signal connection with a suitable antenna. In a further act, a pilot tone receiver receives the pilot tone signal. The pilot tone receiver may to this end have an antenna or have a signal connection with an antenna, for instance, an antenna coil of a local coil. The pilot tone signal may already be preprocessed here by the antenna, (for instance, amplified, filtered, changed over to another frequency, or digitalized). In another act, the pilot tone receiver selects the pilot tone signal from the signals of the antenna by encoding. To this end, the pilot tone receiver decodes the received signal by the encoding. Depending on the encoding used, for instance, the decoding may take place by a filter or a multiplication with a template which corresponds to the encoding.

In a further act, the pilot tone receiver extracts a physiological parameter from the pilot tone signal by the pilot tone receiver. This may take place by analyzing amplitude and/or phase changes in the received pilot tone signal. It is also conceivable for the pilot tone receiver to receive and evaluate the signals of a number of antennas and in the process to correlate the amplitudes and/or phase changes of a number of antennas.

The pilot tone receiver may advantageously clearly identify the encoded signal of the pilot tone transmitter also with other existing radio frequency signals, so that during operation it is also possible to acquire physiological parameters of the patient without interference.

In one conceivable embodiment of the medical image acquisition device, the electromagnetic radio frequency signal is a spread spectrum signal. Here a spread spectrum signal is considered to be a signal whose output is distributed across a frequency range and may then also be received and decoded by the corresponding receiver by suitable modulation if, in terms of its field strength, the spread spectrum signal remains at least in some frequency ranges below the noise or field strength of interference signals.

A pilot tone signal with a spread spectrum distribution advantageously enables a transmission of the pilot tone signal, without interfering with other radio frequency signals of the medical image acquisition device, by the pilot tone signal being able to remain below a noise level.

In one possible embodiment of the medical image acquisition device, the code is a pseudo random code. A pseudo random code is understood here to refer to a code which generates a uniform spectral distribution of the signal modulated with the code, comparable with white noise. Furthermore, a series of numbers of the pseudo random code repeats at the earliest after 50, 100, 500, or 1000 characters.

A pseudo random code advantageously allows for a reliable autocorrelation of the received signal and thus for a phase relationship to be established between the transmitted and received pilot tone signal.

In one conceivable embodiment of the medical image acquisition device, the pilot tone transmitter modulates the electromagnetic radio frequency signal with a type of modulation from amplitude modulation, frequency modulation, or phase modulation the code onto the radio frequency signal. Other mixed forms such as square phase modulations are conceivable.

Phase and frequency modulation advantageously enable a modulation unaffected by disruptive amplitude fluctuations, while an amplitude fluctuation allows for a simple demodulation.

In one possible embodiment, the medical image acquisition device is a magnetic resonance tomograph. Here the pilot tone signal may lie in a different frequency range to that of the magnetic resonance signals, in an immediately adjacent frequency range, so that the same or shared radio frequency components may be used for pilot tone and magnetic resonance signal, or may even use the same frequency band of the Larmor frequency. It is also conceivable here for the pilot tone receiver to be one of the receivers for magnetic resonance signals, the output signal of which is decoded in a special way.

Magnetic resonance tomographs operate with a plurality of radio frequency signals. A pilot tone signal which is resistant on the one hand to interferences from other signals, but on the other hand may also transmit below the noise limit and thus also without significant disruption to the magnetic resonance signal, is particularly advantageous in this application.

In one conceivable embodiment of the magnetic resonance tomograph, the pilot tone transmitter is configured to generate an electromagnetic radio frequency signal orthogonally to a magnetic resonance signal to be acquired by the magnetic resonance tomograph. A pilot tone signal, the detection of which is unaffected by the magnetic resonance signal, is referred to here as orthogonal.

An orthogonal pilot tone signal advantageously has less or no interaction with the magnetic resonance signal, so that the monitoring of the physiological parameters with the pilot tone and the image acquisition by a magnetic resonance signal do not interfere with one another.

Here it is conceivable, for instance, for the pilot tone signal in the k-space to assume a surface which is disjointed with the MR signal to be expected, e.g., differs in frequency and/or phase herefrom. The pilot tone transmitter may be configured, for instance, to receive an item of information from the magnetic resonance tomograph which specifies a position of an MR signal in the k-space to be expected, which is to be scanned with the subsequent sequence. The pilot tone transmitter is also configured to generate a pilot tone signal as a function of this item of information, which recesses the surface of the MR signal in the k-space, by the frequency and/or phase being adjusted accordingly, in other words the pilot tone signal from the pilot tone transmitter being modulated accordingly with a code. It is also conceivable here for the pilot tone signal from the pilot tone transmitter to be redetermined in the k-space for each pulse train according to the trajectory.

The disjointed signals in the k-space advantageously allow a pilot tone to be sent and evaluated during the entire sequence, without disrupting the MR signal for the image evaluation and thus continuously monitoring a physiological parameter.

It is also conceivable for the pilot tone signal to be temporally orthogonal to the MR signal. Individual sequences in the MR signal acquisition may last just a few milliseconds. By contrast, the physiological signals to be monitored have frequencies of more than 0.1 second (pulse) up to several seconds (breathing). It is therefore possible to interrupt or weaken the pilot tone signal temporarily during receipt of an MR signal, so that the MR signal may be received undisturbed. Here the pilot tone receiver is configured to receive an item of information relating to the temporal curve of a sequence from the magnetic resonance receiver, wherein the pilot tone transmitter is also configured to generate a pilot tone signal as a function of this item of information, which is weakened or suppressed during the receipt of the MR signal by the amplitude being adjusted accordingly. In other words, the pilot tone signal from the pilot tone transmitter is modulated accordingly with a code.

The different measurement times for the physiological parameters and a pulse train, in particular, because the actually acquired MR signal with the amplitudes present in the phase only assumes a short period of time therefrom, advantageously also allow an interference-free parallel acquisition of image and physiological parameter by a temporal nesting of the pilot tone signal with the pulse sequence.

In one embodiment, the orthogonality may also be provided alternately or in addition on the receiver side. Here the pilot tone receiver may have a filter which filters the pilot tone signal out of a received radio frequency signal. For instance, with the filter with the orthogonality in the k-space may take place by a Fourier transform and selection in the k-space. With a temporal orthogonality, the filter may be embodied by a corresponding temporal weighting. With a by the encoding by a pseudo random code or comparable template, the filter may be realized for instance by an unweighted template multiplication in order to identify the pseudo random code in the pilot tone receiver. The scalar product including the pilot tone identification and MR signal may then be equal to zero. In reality, encodings are used which allow the scalar product with the signal expected from the preinformation (e.g., sequence type, FOV, k-space encoding, preceding measurements) to go to zero. If the pilot tone signal is separated and known in this way, it may also be considered by the receiver for the magnetic resonance signals, by it being subtracted for instance. Here an adaptive filter is also conceivable in the MR signal receiver, which minimize a portion of the pilot tone signal in the MR signal.

An orthogonal pilot tone signal may advantageously also be separated from a magnetic resonance signal by a decoder in the pilot tone receiver, so that the pilot tone signal and the acquisition of a physiological parameter by the pilot tone signal are not disrupted by the image acquisition.

BRIEF DESCRIPTION OF THE DRAWINGS

The above-described properties, features, and advantages of this disclosure and the manner in which these are achieved will now be described in detail, more clearly and explicitly with the following description of the exemplary embodiments, and by reference to the drawings, in which:

FIG. 3 depicts a schematic flow chart of an example of a method.

DETAILED DESCRIPTION

Figure 1:
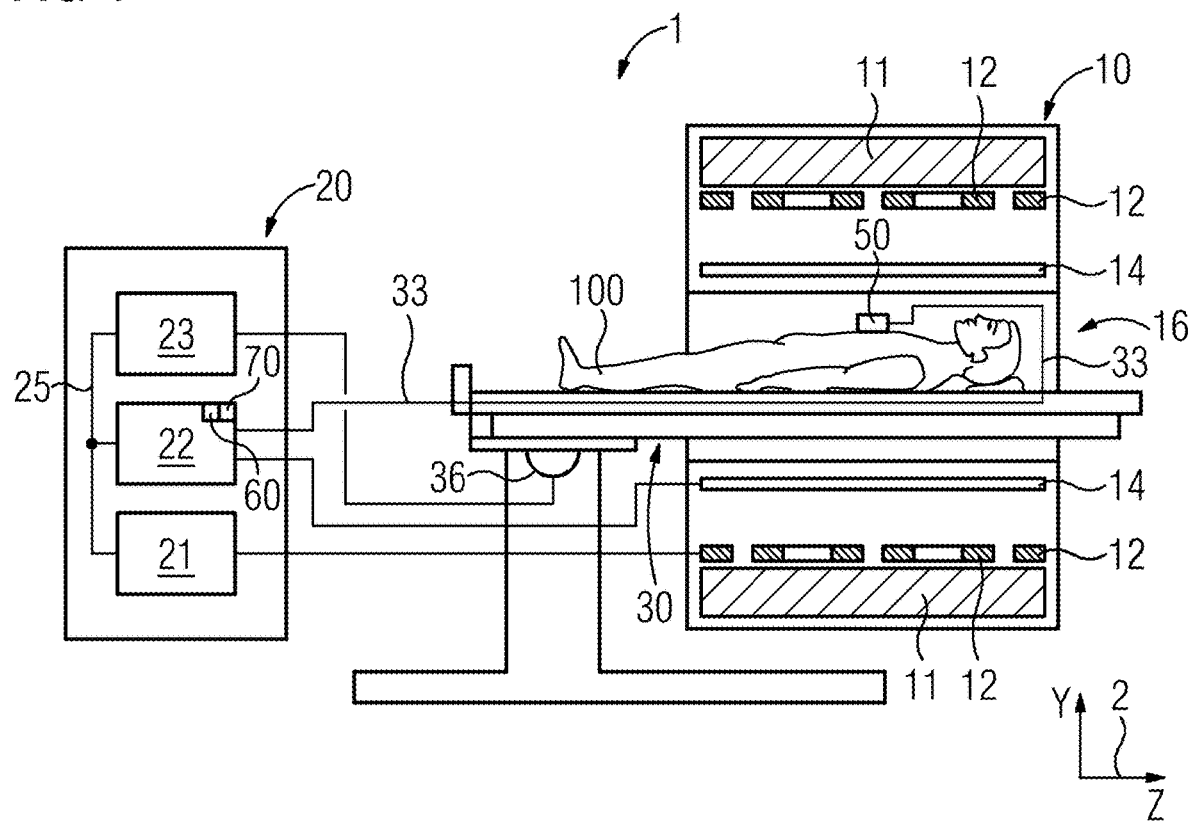
FIG. 1 depicts a schematic display of an example of a magnetic resonance tomograph with a pilot tone transmitter and a pilot tone receiver.

FIG. 1 depicts a schematic display of an embodiment of a magnetic resonance tomograph 1 with a pilot tone transmitter 60 and a pilot tone receiver 70.

The magnet unit 10 has a field magnet 11, which produces a static magnetic field BO for orienting nuclear spins of test persons or of the patient 100 in a recording region. The recording region is characterized by an extremely homogenous static magnetic field BO, wherein the homogeneity relates in particular to the magnetic field strength or the amount. The recording region is virtually spherical and arranged in a patient tunnel 16 which extends in a longitudinal direction 2 through the magnet unit 10. A patient couch 30 may be moved in the patient tunnel 16 by the carriage 36. The field magnet 11 may be a superconducting magnet, which may provide magnetic fields having a magnetic flux density of up to 3 T or even higher in the latest equipment. For lower field strengths, however, permanent magnets or electromagnets having normal-conducting coils may also be used.

The magnet unit 10 further includes gradient coils 12 which are configured, for spatial differentiation of the acquired imaging regions in the examination volume, to overlay variable magnetic fields onto the magnetic field BO in three spatial directions. The gradient coils 12 may be coils made of normal-conducting wires which may generate mutually orthogonal fields in the examination volume.

The magnet unit 10 likewise includes a body coil 14, which is configured to radiate a radio frequency signal supplied via a signal line into the examination volume and to receive resonance signals emitted by the patient 100 and to output said resonance signals via a signal line.

A control unit 20 supplies the magnet unit 10 with the various signals for the gradient coils 12 and the body coil 14 and evaluates the received signals.

Thus, the control unit 20 has a gradient controller 21 configured to supply the gradient coils 12 with variable currents by way of supply lines, which variable currents provide the desired gradient fields in the examination volume on a temporally coordinated basis.

Furthermore, the control unit 20 has a radio frequency unit 22 which is configured to generate a radio frequency pulse with a predetermined temporal sequence, amplitude, and spectral power distribution for the excitation of a magnetic resonance of the nuclear spin in the patient 100. Thereby, pulse power levels in the region of kilowatts may be achieved. The excitation pulses may be radiated into the patient 100 via the body coil 14 or also via a local transmitting antenna.

A controller 23 communicates with the gradient controller 21 and the radio frequency unit 22 by way of a signal bus 25.

A local coil 50 is arranged on the patient 100 and is connected via a connecting line 33 with the radio frequency unit 22 and its receiver.

The radio frequency unit 22 has a pilot tone transmitter 60. The pilot tone transmitter 60 has a signal connection with the local coil 50, which has a transmitting antenna for emitting the pilot tone signal. It is also conceivable to arrange a separate transmitting antenna for the pilot tone signal in the patient tunnel 16 or on the patient 100. It would also be conceivable to arrange the pilot tone transmitter 60 in the local coil 50.

The radio frequency unit 22 has a pilot tone receiver 70. The pilot tone receiver 70 has a signal connection with the local coil 50, which has a receiving antenna for receiving the pilot tone signal. It is also conceivable to arrange a separate receiving antenna for the pilot tone signal in the patient tunnel 16 or on the patient 100. The pilot tone receiver 70 may use one or more antenna coils of the local coil, which are provided to receive the magnetic resonance signal. In this context, it is also conceivable for the pilot tone receiver 70 to be identical to the receivers for the magnetic resonance signal and to only apply some additional processing acts in the form of filters or algorithms to the signal of the antenna coils in order to extract the pilot tone signal. It would also be conceivable to arrange the pilot tone receiver 70 in the local coil 50.

Figure 2:
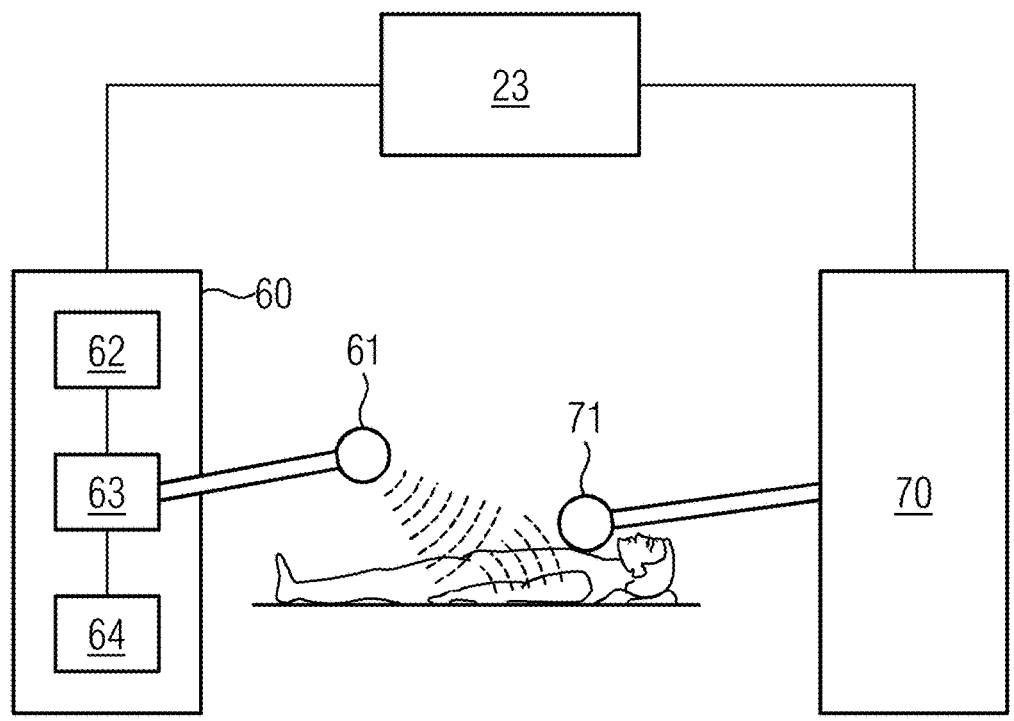
FIG. 2 depicts a schematic display of an example of functional blocks of a magnetic resonance tomograph.

In FIG. 2, the functional units required to detect a physiological parameter using a pilot tone are shown schematically, on the basis of which the functionality of the disclosure is to be explained below.

The pilot tone transmitter 60 generates the pilot tone signal. The pilot tone signal is then radiated into a patient by way of an induction loop 61. To this end, the pilot tone transmitter 60 has an oscillator 62 which generates a radio frequency signal with a suitable frequency. With a magnetic resonance tomograph 1 as a medical image acquisition device, the frequency may be close to or in the frequency range of a Larmor frequency used by the magnetic resonance tomograph 1 during imaging. Instead of the oscillator 62 in the pilot tone transmitter 60, the radio frequency signal may be supplied by the radio frequency unit 22, particularly with a magnetic resonance tomography system 1, or generated from a supplied signal in the pilot tone transmitter, in order to provide a sufficiently high frequency stability particularly with respect to the magnetic resonance signals and to minimize interactions with the image acquisition.

The pilot tone transmitter 60 also has an encoder 64 and a modulator 63, in order to modulate a code generated by the encoder 64 onto the radio frequency signal. Each code may be suited here to allow a unique identification of the pilot tone signal. It is furthermore advantageous if the code has an item of phase information, so that in the receiver explained subsequently, a phase shift is identified, and different propagation paths of the pilot tone signal may be differentiated. With a magnetic resonance tomograph, it is furthermore advantageous if the code generates as statistical a spectral distribution of the signal as possible, in order to prevent image artifacts as a result of individual interfering peaks in the k-space. One possible way of generating such a code is a pseudo random sequence generator as an encoder 64.

The modulator 63 impresses the code onto the radio frequency signal. Modulation methods such as amplitude modulation, frequency modulation, phase modulation, or more complex methods such as square amplitude modulation may be used for instance. The generated pilot tone signal may have a spread spectrum characteristic. Here, a signal is considered to be a spread spectrum signal, the output of which is distributed across a frequency range and may then also be received and decoded by the corresponding receiver by the used modulation if in terms of its field strength the spread spectrum signal remains at least in some frequency ranges below the noise or field strength of interference signals. The spread spectrum technology therefore allows the pilot tone to be transmitted in the frequency range of the magnetic resonance signal with a magnetic resonance tomograph 1 and to remain below its noise level so that the image acquisition is not disrupted by the pilot tone signal. The same frequency in turn allows components such as antenna coils and receivers of the magnetic resonance tomograph also to be used for receiving the pilot tone signal. The pilot tone signal is therefore made orthogonal to the magnetic resonance signal by the encoding.

With a magnetic resonance tomograph 1, an orthogonality may however also be produced between the magnetic resonance signal and the pilot tone signal, by the radio frequency signal in the phase and frequency angle being embodied so that in the k-space it assumes in each case disjointed surfaces with respect to the magnetic resonance signal to be expected with the respective pulse sequence of the trajectory. For instance, the controller 23 may send corresponding information to the oscillator 62 or the encoder 64 by way of the pulse sequence, so that the radio frequency signal is generated with corresponding frequency and phase angle or the pilot tone signal is brought into this by the modulation. Alternatively, the radio frequency signal may already be provided accordingly to the pilot tone transmitter 60 by the radio frequency unit 22.

A temporal orthogonality is also conceivable with a magnetic resonance tomograph 1. Within a pulse draw, the magnetic resonance signal is only acquired during a short period of time of a few milliseconds if the phases of the individual nuclear spins interfere constructively. During the remaining time of the pulse draw, no meaningful signal is to be acquired for an imaging, because the signals originate from regions distributed across the space. The physiological parameters such as heartbeat or breathing by contrast may change in periods of time of 0.1 second up to a number of seconds. The physiological parameters may therefore also be acquired if the pilot tone signal is reduced or suppressed while the magnetic resonance signals are acquired. To this end, it is conceivable for instance for the controller 23 of the magnetic resonance tomograph 1 to send a corresponding signal to the pilot tone transmitter 60 and thereupon for the latter to suppress the pilot tone. With a generation of the radio frequency signal by the radio frequency unit 22, it is also conceivable that the latter interrupts the generation based on the instruction of the controller.

The pilot tone signal emitted by the induction coil 61 then propagates in the patient tunnel 16 and reaches the antenna coil 51 via different paths, sometimes through the patient, sometimes directly. As a result of the absorption and phase shift which change temporally with the physiological parameters and also as a result of the thus changing interference of waves of the pilot tone signal arriving via different propagation paths, a current which changes in terms of amplitude and/or phase with the physiological parameters is induced in the antenna coil 71. If the antenna coil 71 is one of several antenna coils, for instance, in the case of a local coil 50 with an antenna matrix, the amplitude and/or phase of a number of spatially distributed locations may furthermore also be acquired and evaluated.

The signal of the antenna coil 71 is fed to the pilot tone receiver 70, which may amplify and preprocess the signal, e.g., apply a band pass filter. A demodulation complementary to the type of modulation used then takes place. A decoding also takes place according to the encoding used in the pilot tone transmitter 60. For an encoding with a pseudo random sequence, a corresponding autocorrelation is carried out, with which the pilot tone signal is selected and an item of information relating to a phase angle may also be determined. With scalar multiplication of the received signal with the template of the pseudo random sequence, the pilot tone signal is therefore separated in the case of a correct phase angle.

With an encoding by frequency and/or phase angle in the k-space, the pilot tone receiver may for instance obtain an item of information from the controller 23 relating to the frequency and/or phase used by the pilot tone transmitter as a function of the trajectory or the pulse draw and select the corresponding signal with a filter in the k-space. In conjunction with a pseudo random sequence, an autocorrelation in the k-space would also be conceivable in order to select the pilot tone signal.

With a temporal encoding of the pilot tone signal, it is in turn conceivable for the pilot tone receiver 70, as a function of a signal of the controller 23, to suppress the input signal in synchrony with the pulse draw, if the magnetic resonance signal is to be expected.

The pilot tone receiver 70 evaluates the pilot tone signal separated from the MR signals on the physiological parameters. Here, frequency-dependent and time-dependent filters may be used and/or an adjustment (e.g., fitting) to predetermined measuring curves of comparable physiological processes may take place in order to extract a physiological parameter from the pilot tone signal. For instance, different temporal curves of the pilot tone may be recorded while simultaneously measuring the breathing by chest belts or of the heartbeat while simultaneously recording an ECG, in order then subsequently also to determine the physiological parameters such as point in time relative to the breathing cycle or heartbeat by using artificial intelligence algorithms from the pilot tone signal.

The pilot tone receiver 70 may be embodied as a separate unit or as part of the image acquisition device. In particular, with a magnetic resonance tomograph 1 with antennas and receivers of the radio frequency unit 22 and a pilot tone signal in the frequency range of the magnetic resonance signal, it is possible to use the receivers available for the MR signal also for the pilot tone. With a digital signal processing, it is also conceivable to implement the previously described filter and autocorrelation and decoding algorithms as software on a signal processor or FPGA. It is also conceivable to allow an algorithm for determining the physiological parameter to be executed in the image evaluation or the controller 23.

FIG. 3 depicts an exemplary flow chart for a method for operating a medical image acquisition device and determining a physiological parameter using a pilot tone with identification.

In act S10, a radio frequency signal is made available for the pilot tone. The radio frequency signal may be provided by an oscillator 62 of the pilot tone transmitter 60. The radio frequency signal may also be fed to the pilot tone transmitter 60 from a radio frequency unit 22 of a magnetic resonance tomograph 1 for instance.

In act S20, the pilot tone transmitter generates a pilot tone signal from the radio frequency signal by modulation in a modulator 63 with a code. The code is provided by an encoder 64.

The code may be a pseudo random code, for instance, which is generated with an algorithm from a start value. The code may have a uniform, spectral distribution comparable with white noise. Furthermore, the pseudo random code may be configured for more than 50, 100, 250, 500, 1000 or more characters without repetition, so that a time window for different runtimes of the pilot tone signal is sufficiently large in the subsequent encoding in order to provide a unique phase relationship.

The code may also be embodied so that by modulation the pilot tone assumes a predetermined surface in the k-space. Here the controller 23 may set the encoder 64 so that the pilot tone signal in the k-space assumes a disjointed surface with respect to the MR signal to be expected. In one case, this may be another frequency, or however also a frequency/phase combination. By a suitable type of modulation, such as frequency modulation, a corresponding distribution for the pilot tone may then be achieved in the k-space by way of the encoding. A pilot tone signal, which is orthogonal in the k-space, may be provided in this way.

In act S30, the pilot tone signal is emitted into a body of a patient. To this end, an additional antenna may be provided as an antenna in the patient tunnel or the local coil. It is also conceivable, however, for an antenna coil of a local coil 50, which is positioned outside of the field of view, or for another reason is not used to receive the MR signal, to be used as an induction loop 61 for the pilot tone signal.

In a further act S40, the pilot tone signal is received with the pilot tone receiver 70. One or more antenna coils of the local coil 50 may be used here as antenna coils, but separate antenna coils 71 are however also conceivable for the pilot tone signal, particularly if the image acquisition device is not a magnetic resonance tomograph 1. The receiving may also include a preamplification, filtering, frequency changeover, and/or digitalization of the pilot tone signal.

In act S50, the pilot tone receiver selects the pilot tone signal using encoding. With an encoding with a pseudo random series of numbers, a scalar multiplication with a template of the pseudo random series of numbers may be provided by a decoder, which only supplies an output signal for the encoded signal with the correct phase angle. Other strings which are autocorrelating and orthogonal to the MR signal are conceivable, such as strings generated with the aid of resorting algorithms such as bit change or not equally distributed random sequences such as colored or gaussian noise.

With a frequency/phase encoding in the k-space, temporally variable filters may in turn be provided in the k-space in order to separate the pilot tone signal from the MR signals after an FFT.

With a temporal encoding, a temporally variable weighting is in turn suited to separating the signals in the pilot tone receiver. The controller 23 here identifies the course of the pulse sequence and may predetermine the time window for decoding the temporal encoding to the pilot tone receiver.

The pilot tone receiver here may also forward the separated pilot tone signal to a following image evaluation in a magnetic resonance tomograph 1, so that the known pilot tone signal in the MR signals may be subtracted and suppressed.

In act S60, the pilot tone receiver 70 extracts a physiological parameter from the pilot tone signal. This may, as already shown, be carried out by simple amplitude modulation by way of fitting signal curves until the pilot tone signal is analyzed with a network trained by artificial intelligence.

Although the disclosure has been illustrated and described in detail with the exemplary embodiments, the disclosure is not restricted by the examples given, and a person skilled in the art may derive other variations therefrom without departing from the protective scope of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A magnetic resonance tomograph comprising:
   a pilot tone transmitter configured to emit an electromagnetic radio frequency signal into a patient; and
   a pilot tone receiver configured to receive the electromagnetic radio frequency signal and to decode an item of information about a physiological process in the patient,
   wherein the pilot tone transmitter has a modulator configured to modulate the electromagnetic radio frequency signal with a code and the pilot tone receiver is configured to select the modulated electromagnetic radio frequency signal by an encoding from a plurality of signals, and
   wherein the electromagnetic radio frequency signal lies in an immediately adjacent frequency range or in a same frequency range as that of a magnetic resonance signal to be acquired by the magnetic resonance tomograph such that the pilot tone receiver is configured to receive both the electromagnetic radio frequency signal and the magnetic resonance signal.

2. The magnetic resonance tomograph of claim 1, wherein the electromagnetic radio frequency signal is a spread spectrum signal.

3. The magnetic resonance tomograph of claim 2, wherein the code is a pseudo random code.

4. The magnetic resonance tomograph of claim 3, wherein the pilot tone transmitter is configured to modulate the electromagnetic radio frequency signal by amplitude modulation, frequency modulation, or phase modulation.

5. The magnetic resonance tomograph of claim 1, wherein the pilot tone transmitter is configured to generate the electromagnetic radio frequency signal orthogonally to the magnetic resonance signal to be acquired from the magnetic resonance tomograph such that the electromagnetic radio frequency signal does not interfere with the magnetic resonance signal.

6. The magnetic resonance tomograph of claim 5, wherein the pilot tone transmitter is configured to generate the electromagnetic radio frequency signal in a k-space orthogonally to the magnetic resonance signal to be acquired from the magnetic resonance tomograph.

7. The magnetic resonance tomograph of claim 5, wherein the pilot tone transmitter is configured to generate the electromagnetic radio frequency signal temporally orthogonally to the magnetic resonance signal to be acquired from the magnetic resonance tomograph.

8. The magnetic resonance tomograph of claim 1, wherein the pilot tone receiver has a decoder which is orthogonal to the magnetic resonance signal to be acquired from the magnetic resonance tomograph such that detection of the electromagnetic radio frequency signal is unaffected by the magnetic resonance signal.

9. The magnetic resonance tomograph of claim 1, wherein the code is a pseudo random code.

10. The magnetic resonance tomograph of claim 1, wherein the pilot tone transmitter is configured to modulate the electromagnetic radio frequency signal by amplitude modulation, frequency modulation, or phase modulation.

11. The magnetic resonance tomograph of claim 1, wherein the pilot tone transmitter is configured to generate the electromagnetic radio frequency signal orthogonally to the magnetic resonance signal to be acquired from the magnetic resonance tomograph such that the electromagnetic radio frequency signal does not interfere with the magnetic resonance signal.

12. The magnetic resonance tomograph of claim 1, wherein the pilot tone transmitter is configured to generate the electromagnetic radio frequency signal in a k-space orthogonally to the magnetic resonance signal to be acquired from the magnetic resonance tomograph such that the electromagnetic radio frequency signal does not interfere with the magnetic resonance signal.

13. The magnetic resonance tomograph of claim 1, wherein the pilot tone transmitter is configured to generate the electromagnetic radio frequency signal temporally orthogonally to the magnetic resonance signal to be acquired from the magnetic resonance tomograph such that the electromagnetic radio frequency signal does not interfere with the magnetic resonance signal.

14. The magnetic resonance tomograph of claim 1, wherein the pilot tone receiver has a decoder which is orthogonal to the magnetic resonance signal to be acquired from the magnetic resonance tomograph such that detection of the electromagnetic radio frequency signal is unaffected by the magnetic resonance signal.

15. The magnetic resonance tomograph of claim 1, wherein the same frequency range comprises a Larmor frequency used by the magnetic resonance tomograph during imaging.

16. A method for operating a magnetic resonance tomograph, the method comprising:
    providing a radio frequency signal;
    generating a pilot tone signal by modulating the radio frequency signal with a code by a pilot tone transmitter of the magnetic resonance tomograph;
    emitting the pilot tone signal into a body of a patient by the pilot tone transmitter;
    receiving the pilot tone signal with a pilot tone receiver;
    receiving a magnetic resonance signal with the pilot tone receiver, wherein the pilot tone signal lies in an immediately adjacent frequency range or in a same frequency range as that of the magnetic resonance signal;
    selecting, by the pilot tone receiver, the pilot tone signal by an encoding from a plurality of signals; and
    extracting a physiological parameter from the pilot tone signal by the pilot tone receiver.

17. A computer-readable storage medium comprising electronically readable control information stored thereon, wherein the electronically readable control information is configured to be used in a controller of a magnetic resonance tomograph, and wherein the electronically readable control information is configured to cause the magnetic resonance tomograph to:
    provide a radio frequency signal;
    generate a pilot tone signal by modulating the radio frequency signal with a code by a pilot tone transmitter of the magnetic resonance tomograph;
    emit the pilot tone signal into a body of a patient by the pilot tone transmitter;
    receive the pilot tone signal with a pilot tone receiver;
    receive a magnetic resonance signal with the pilot tone receiver, wherein the pilot tone signal lies in an immediately adjacent frequency range or in a same frequency range as that of the magnetic resonance signal;
    select the pilot tone signal by an encoding from a plurality of signals; and
    extract a physiological parameter from the pilot tone signal by the pilot tone receiver.

* * * * *